(12) United States Patent
Zivitz et al.

(10) Patent No.: US 10,311,209 B2
(45) Date of Patent: *Jun. 4, 2019

(54) DEVICE AND METHOD FOR INSULIN DOSING

(75) Inventors: Maury Zivitz, Indianapolis, IN (US); Lois Jovanovic, Santa Barbara, CA (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 1760 days.

This patent is subject to a terminal disclaimer.

(21) Appl. No.: 13/545,512

(22) Filed: Jul. 10, 2012

(65) Prior Publication Data

US 2013/0184996 A1    Jul. 18, 2013

Related U.S. Application Data

(63) Continuation of application No. 11/422,639, filed on Jun. 7, 2006, now Pat. No. 8,251,904.

(60) Provisional application No. 60/689,303, filed on Jun. 9, 2005, provisional application No. 60/689,166, filed on Jun. 9, 2005, provisional application No. 60/689,751, filed on Jun. 9, 2005, provisional application No. 60/689,703, filed on Jun. 9, 2005, provisional application No. 60/689,702, filed on Jun. 9, 2005.

(51) Int. Cl.
*G01N 33/48*    (2006.01)
*G06F 19/00*    (2018.01)
*A61B 5/00*    (2006.01)
*A61B 5/145*    (2006.01)

(52) U.S. Cl.
CPC ........ *G06F 19/3456* (2013.01); *A61B 5/0002* (2013.01); *A61B 5/14532* (2013.01)

(58) Field of Classification Search
None
See application file for complete search history.

(56) References Cited

U.S. PATENT DOCUMENTS

| | | | |
|---|---|---|---|
| 4,731,726 A * | 3/1988 | Allen, III | A61B 5/14532 128/920 |
| 5,216,597 A | 6/1993 | Beckers | |
| 5,251,126 A | 10/1993 | Kahn et al. | |
| 5,307,263 A | 4/1994 | Brown | |
| 5,420,108 A | 5/1995 | Shohet | |
| 5,434,611 A | 7/1995 | Tamura | |
| 5,441,047 A | 8/1995 | David et al. | |
| 5,459,317 A | 10/1995 | Small et al. | |
| 5,558,638 A | 9/1996 | Evers et al. | |
| 5,576,952 A | 11/1996 | Stutman et al. | |
| 5,589,045 A | 12/1996 | Hyodo | |
| 5,601,435 A | 2/1997 | Quy | |
| 5,626,144 A | 5/1997 | Tacklind et al. | |
| 5,633,910 A | 5/1997 | Cohen | |
| 5,678,562 A | 10/1997 | Sellers | |

(Continued)

FOREIGN PATENT DOCUMENTS

| | | |
|---|---|---|
| CA | 2125300 | 11/1995 |
| DE | 4315531 | 12/1992 |

(Continued)

*Primary Examiner* — Larry D Riggs, II
(74) *Attorney, Agent, or Firm* — Faegre Baker Daniels LLP

(57) ABSTRACT

A device and method of providing instruction to a patient regarding the dosing of insulin is provided.

19 Claims, 3 Drawing Sheets

(56) References Cited

U.S. PATENT DOCUMENTS

| | | |
|---|---|---|
| 5,678,571 A | 10/1997 | Brown |
| 5,730,654 A | 3/1998 | Brown |
| 5,752,976 A | 5/1998 | Duffin et al. |
| 5,781,455 A | 7/1998 | Hyodo |
| 5,822,715 A | 10/1998 | Worthington et al. |
| 5,828,943 A | 10/1998 | Brown |
| 5,832,448 A | 11/1998 | Brown |
| 5,867,688 A | 2/1999 | Simmon et al. |
| 5,872,713 A | 2/1999 | Douglas et al. |
| 5,879,163 A | 3/1999 | Brown et al. |
| 5,887,133 A | 3/1999 | Brown et al. |
| 5,897,493 A | 4/1999 | Brown |
| 5,899,855 A | 5/1999 | Brown |
| 5,913,310 A | 6/1999 | Brown |
| 5,918,603 A | 7/1999 | Brown |
| 5,919,141 A | 7/1999 | Money et al. |
| 5,919,216 A | 7/1999 | Houben et al. |
| 5,933,136 A | 8/1999 | Brown |
| 5,940,801 A | 8/1999 | Brown |
| 5,950,630 A | 9/1999 | Portwood et al. |
| 5,951,300 A | 9/1999 | Brown |
| 5,956,501 A | 9/1999 | Brown |
| 5,960,403 A | 9/1999 | Brown |
| 5,967,975 A | 10/1999 | Ridgeway |
| 5,985,559 A | 11/1999 | Brown |
| 5,997,476 A | 12/1999 | Brown |
| 6,024,699 A | 2/2000 | Surwit et al. |
| 6,032,119 A | 2/2000 | Brown et al. |
| 6,068,615 A | 5/2000 | Brown et al. |
| 6,101,478 A | 8/2000 | Brown |
| 6,116,148 A | 9/2000 | Allen |
| 6,117,076 A | 9/2000 | Cassidy |
| 6,131,090 A | 10/2000 | Basso, Jr. et al. |
| 6,134,504 A | 10/2000 | Douglas et al. |
| 6,144,837 A | 11/2000 | Quy |
| 6,144,922 A | 11/2000 | Douglas et al. |
| 6,151,586 A | 11/2000 | Brown |
| 6,161,095 A | 12/2000 | Brown |
| 6,162,180 A | 12/2000 | Miesel et al. |
| 6,167,362 A | 12/2000 | Brown et al. |
| 6,168,563 B1 | 1/2001 | Brown |
| 6,186,145 B1 | 2/2001 | Brown |
| 6,192,891 B1 | 2/2001 | Gravel et al. |
| D439,242 S | 3/2001 | Brown et al. |
| 6,196,970 B1 | 3/2001 | Brown |
| 6,210,272 B1 | 4/2001 | Brown |
| 6,216,096 B1 | 4/2001 | Obermeier |
| 6,233,539 B1 | 5/2001 | Brown |
| 6,246,966 B1 | 6/2001 | Perry |
| 6,246,992 B1 | 6/2001 | Brown |
| 6,248,065 B1 | 6/2001 | Brown |
| 6,260,022 B1 | 7/2001 | Brown |
| 6,264,614 B1 | 7/2001 | Albert et al. |
| 6,269,314 B1 | 7/2001 | Iitawaki et al. |
| 6,270,455 B1 | 8/2001 | Brown |
| 6,270,457 B1 | 8/2001 | Bardy |
| 6,277,071 B1 | 8/2001 | Hennessy et al. |
| 6,280,380 B1 | 8/2001 | Bardy |
| 6,290,646 B1 | 9/2001 | Cosentino et al. |
| 6,292,698 B1 | 9/2001 | Duffin et al. |
| 6,295,506 B1 | 9/2001 | Heinonen et al. |
| 6,309,884 B1 | 10/2001 | Cooper et al. |
| 6,311,163 B1 | 10/2001 | Sheehan et al. |
| 6,315,719 B1 | 11/2001 | Rode et al. |
| 6,330,426 B2 | 12/2001 | Brown et al. |
| 6,334,778 B1 | 1/2002 | Brown |
| 6,352,505 B1 | 3/2002 | Bortz |
| 6,364,834 B1 | 4/2002 | Reuss et al. |
| 6,368,273 B1 | 4/2002 | Brown |
| 6,375,469 B1 | 4/2002 | Brown |
| 6,377,894 B1 | 4/2002 | Deweese et al. |
| 6,379,301 B1 | 4/2002 | Worthington et al. |
| 6,381,577 B1 | 4/2002 | Brown |
| 6,401,085 B1 | 6/2002 | Gershman et al. |
| 6,402,691 B1 | 6/2002 | Peddicord et al. |
| 6,406,426 B1 | 6/2002 | Reuss et al. |
| 6,424,996 B1 | 7/2002 | Killcommons et al. |
| 6,442,432 B2 | 8/2002 | Lee |
| 6,442,433 B1 | 8/2002 | Linberg |
| 6,454,705 B1 | 9/2002 | Cosentino et al. |
| 6,471,645 B1 | 10/2002 | Warkentin et al. |
| 6,493,747 B1 | 12/2002 | Simmon et al. |
| 6,497,655 B1 | 12/2002 | Linberg et al. |
| 6,505,059 B1 | 1/2003 | Kollias et al. |
| 6,507,868 B2 | 1/2003 | Simmon et al. |
| 6,512,986 B1 | 1/2003 | Harmon |
| 6,540,672 B1 | 4/2003 | Simonsen et al. |
| 6,544,173 B2 | 4/2003 | West et al. |
| 6,551,276 B1 | 4/2003 | Mann et al. |
| 6,554,798 B1 | 4/2003 | Mann et al. |
| 6,558,320 B1 | 5/2003 | Causey, III et al. |
| 6,558,321 B1 | 5/2003 | Burd et al. |
| 6,561,978 B1 | 5/2003 | Conn et al. |
| 6,571,294 B2 | 5/2003 | Simmon et al. |
| 6,577,901 B2 | 6/2003 | Thompson |
| 6,579,242 B2 | 6/2003 | Bui et al. |
| 6,582,366 B1 | 6/2003 | Porumbescu |
| 6,589,229 B1 | 7/2003 | Connelly et al. |
| 6,598,084 B1 | 7/2003 | Edwards et al. |
| 6,599,250 B2 | 7/2003 | Webb et al. |
| 6,604,050 B2 | 8/2003 | Trippel et al. |
| 6,612,984 B1 | 9/2003 | Kerr, II |
| 6,633,772 B2 | 10/2003 | Ford et al. |
| 6,641,533 B2 | 11/2003 | Causey, III et al. |
| 6,650,951 B1 | 11/2003 | Jones et al. |
| 6,656,114 B1 | 12/2003 | Poulsen et al. |
| 6,681,003 B2 | 1/2004 | Linder et al. |
| 6,685,633 B2 | 2/2004 | Albert et al. |
| 6,694,177 B2 | 2/2004 | Eggers et al. |
| 6,705,990 B1 | 3/2004 | Gallant et al. |
| 6,723,045 B2 | 4/2004 | Cosentino et al. |
| 6,723,046 B2 | 4/2004 | Lichtenstein et al. |
| 6,735,479 B2 | 5/2004 | Fabian et al. |
| 6,744,350 B2 | 6/2004 | Blomquist |
| 6,755,783 B2 | 6/2004 | Cosentino et al. |
| 6,783,492 B2 | 8/2004 | Dominguez et al. |
| 6,804,558 B2 | 10/2004 | Haller et al. |
| 6,805,667 B2 | 10/2004 | Christopherson et al. |
| 6,820,057 B1 | 11/2004 | Loch et al. |
| 6,824,512 B2 | 11/2004 | Warkentin et al. |
| 6,968,375 B1 | 11/2005 | Brown |
| 6,980,958 B1 | 12/2005 | Surwit et al. |
| 7,041,468 B2 | 5/2006 | Drucker et al. |
| 7,291,107 B2 | 11/2007 | Hellwig et al. |
| 7,553,281 B2 | 6/2009 | Hellwig et al. |
| 7,769,600 B2 | 8/2010 | Iliff |
| 7,785,313 B2 | 8/2010 | Mastrototaro |
| 7,869,851 B2 | 1/2011 | Hellwig et al. |
| 2001/0011224 A1 | 8/2001 | Brown |
| 2001/0013006 A1 | 8/2001 | Brown |
| 2001/0016310 A1 | 8/2001 | Brown et al. |
| 2001/0021801 A1 | 9/2001 | Bardy |
| 2001/0023315 A1 | 9/2001 | Flach et al. |
| 2001/0031997 A1 | 10/2001 | Lee |
| 2001/0032278 A1 | 10/2001 | Brown et al. |
| 2001/0037060 A1 | 11/2001 | Thompson et al. |
| 2001/0039503 A1 | 11/2001 | Chan et al. |
| 2001/0047252 A1 | 11/2001 | Brown |
| 2001/0049096 A1 | 12/2001 | Brown |
| 2001/0051787 A1 | 12/2001 | Haller et al. |
| 2001/0056229 A1 | 12/2001 | Cosentino et al. |
| 2001/0056328 A1 | 12/2001 | Trippel et al. |
| 2002/0010596 A1 | 1/2002 | Matory |
| 2002/0013613 A1 | 1/2002 | Haller et al. |
| 2002/0013614 A1 | 1/2002 | Thompson |
| 2002/0016530 A1 | 2/2002 | Brown |
| 2002/0019707 A1 | 2/2002 | Cohen et al. |
| 2002/0019748 A1 | 2/2002 | Brown |
| 2002/0026223 A1 | 2/2002 | Riff et al. |
| 2002/0028989 A1 | 3/2002 | Pelletier et al. |
| 2002/0028995 A1 | 3/2002 | Mault |
| 2002/0040208 A1 | 4/2002 | Flaherty et al. |
| 2002/0045804 A1 | 4/2002 | Christopherson et al. |
| 2002/0052539 A1 | 5/2002 | Haller et al. |

(56) References Cited

U.S. PATENT DOCUMENTS

| | | |
|---|---|---|
| 2002/0065682 A1 | 5/2002 | Goldenberg |
| 2002/0072858 A1 | 6/2002 | Cheng |
| 2002/0081559 A1 | 6/2002 | Brown et al. |
| 2002/0082665 A1 | 6/2002 | Haller et al. |
| 2002/0096543 A1 | 7/2002 | Juselius |
| 2002/0099283 A1 | 7/2002 | Christ et al. |
| 2002/0107452 A1 | 8/2002 | Kwong |
| 2002/0120201 A1 | 8/2002 | Chio et al. |
| 2002/0133377 A1 | 9/2002 | Brown |
| 2002/0138017 A1 | 9/2002 | Bui et al. |
| 2002/0143576 A1 | 10/2002 | Nolvak et al. |
| 2002/0156384 A1 | 10/2002 | Eggers et al. |
| 2002/0158775 A1 | 10/2002 | Wallace |
| 2002/0173704 A1 | 11/2002 | Schulze et al. |
| 2002/0183976 A1 | 12/2002 | Pearce |
| 2002/0186821 A1 | 12/2002 | Eggers |
| 2002/0188477 A1 | 12/2002 | Ackermann et al. |
| 2002/0193679 A1 | 12/2002 | Malave et al. |
| 2002/0198445 A1 | 12/2002 | Dominguez et al. |
| 2003/0003522 A1 | 1/2003 | Goldman |
| 2003/0011646 A1 | 1/2003 | Levine et al. |
| 2003/0032077 A1 | 2/2003 | Itoh et al. |
| 2003/0032867 A1 | 2/2003 | Crothall et al. |
| 2003/0032868 A1 | 2/2003 | Graskov et al. |
| 2003/0040821 A1 | 2/2003 | Case |
| 2003/0040824 A1 | 2/2003 | Feige et al. |
| 2003/0041866 A1 | 3/2003 | Linberg et al. |
| 2003/0054428 A1 | 3/2003 | Monfre et al. |
| 2003/0055606 A1 | 3/2003 | Christ et al. |
| 2003/0065536 A1 | 4/2003 | Hansen et al. |
| 2003/0069752 A1 | 4/2003 | LeDain et al. |
| 2003/0069753 A1 | 4/2003 | Brown |
| 2003/0100040 A1 | 5/2003 | Bonnecaze et al. |
| 2003/0105403 A1 | 6/2003 | Istvan et al. |
| 2003/0130590 A1 | 7/2003 | Bui et al. |
| 2003/0139785 A1 | 7/2003 | Riff et al. |
| 2003/0158707 A1 | 8/2003 | Doi |
| 2003/0163351 A1 | 8/2003 | Brown et al. |
| 2003/0176774 A1 | 9/2003 | Hickle et al. |
| 2003/0177177 A1 | 9/2003 | Oka et al. |
| 2003/0179292 A1 | 9/2003 | Provost et al. |
| 2003/0211617 A1 | 11/2003 | Jones |
| 2003/0212317 A1 | 11/2003 | Kovatchev et al. |
| 2003/0212379 A1 | 11/2003 | Bylund et al. |
| 2003/0212579 A1 | 11/2003 | Brown et al. |
| 2003/0216628 A1 | 11/2003 | Bortz et al. |
| 2003/0229514 A2 | 12/2003 | Brown |
| 2004/0006278 A1 | 1/2004 | Webb et al. |
| 2004/0015102 A1 | 1/2004 | Cummings et al. |
| 2004/0019259 A1 | 1/2004 | Brown et al. |
| 2004/0034288 A1 | 2/2004 | Hennessy et al. |
| 2004/0039255 A1 | 2/2004 | Simonsen et al. |
| 2004/0039261 A1 | 2/2004 | Bardy |
| 2004/0039264 A1 | 2/2004 | Bardy |
| 2004/0039606 A1 | 2/2004 | Loch et al. |
| 2004/0044272 A1 | 3/2004 | Moerman et al. |
| 2004/0049355 A1 | 3/2004 | Maus et al. |
| 2004/0054263 A1 | 3/2004 | Moerman et al. |
| 2004/0054352 A1 | 3/2004 | Adams et al. |
| 2004/0059201 A1 | 3/2004 | Ginsberg |
| 2004/0059599 A1 | 3/2004 | McIvor |
| 2004/0068230 A1 | 4/2004 | Estes et al. |
| 2004/0073095 A1 | 4/2004 | Causey, III et al. |
| 2004/0077995 A1 | 4/2004 | Ferek-Petric et al. |
| 2004/0078065 A1 | 4/2004 | Kroll |
| 2004/0078219 A1 | 4/2004 | Kaylor et al. |
| 2004/0087845 A1 | 5/2004 | Katarow et al. |
| 2004/0093167 A1 | 5/2004 | Braig et al. |
| 2004/0093239 A1 | 5/2004 | Ott et al. |
| 2004/0102683 A1 | 5/2004 | Khanuja et al. |
| 2004/0102685 A1 | 5/2004 | Cosentino et al. |
| 2004/0106855 A1 | 6/2004 | Brown |
| 2004/0107116 A1 | 6/2004 | Brown |
| 2004/0116780 A1 | 6/2004 | Brown |
| 2004/0117207 A1 | 6/2004 | Brown |
| 2004/0117208 A1 | 6/2004 | Brown |
| 2004/0117209 A1 | 6/2004 | Brown |
| 2004/0117210 A1 | 6/2004 | Brown |
| 2004/0122353 A1 | 6/2004 | Shahmirian et al. |
| 2004/0122701 A1 | 6/2004 | Dahlin et al. |
| 2004/0126832 A1 | 7/2004 | Wang et al. |
| 2004/0128162 A1 | 7/2004 | Schlotterbeck et al. |
| 2004/0130446 A1 | 7/2004 | Chen et al. |
| 2004/0133455 A1 | 7/2004 | McMahon |
| 2004/0142403 A1 | 7/2004 | Hetzel et al. |
| 2004/0146149 A1 | 7/2004 | Rogers et al. |
| 2004/0147034 A1 | 7/2004 | Gore et al. |
| 2004/0147979 A1 | 7/2004 | Bardy |
| 2004/0148199 A1 | 7/2004 | Dixon, Jr. |
| 2004/0152956 A1 | 8/2004 | Korman |
| 2004/0158232 A1 | 8/2004 | Schetky et al. |
| 2004/0167464 A1 | 8/2004 | Ireland et al. |
| 2004/0193377 A1 | 9/2004 | Brown |
| 2004/0199221 A1 | 10/2004 | Fabian et al. |
| 2004/0199409 A1 | 10/2004 | Brown |
| 2004/0210458 A1 | 10/2004 | Evans et al. |
| 2004/0215049 A1 | 10/2004 | Zdeblick et al. |
| 2004/0215089 A1 | 10/2004 | Bergelson et al. |
| 2004/0215490 A1 | 10/2004 | Duchon et al. |
| 2004/0219500 A1 | 11/2004 | Brown et al. |
| 2004/0225199 A1 | 11/2004 | Evanyk et al. |
| 2004/0225533 A1 | 11/2004 | Cosentino et al. |
| 2004/0249250 A1 | 12/2004 | McGee et al. |
| 2004/0252031 A1 | 12/2004 | Taylor |
| 2004/0254434 A1 | 12/2004 | Goodnow et al. |
| 2004/0260156 A1 | 12/2004 | David et al. |
| 2004/0260189 A1 | 12/2004 | Eggers et al. |
| 2004/0260233 A1 | 12/2004 | Garibotto et al. |
| 2004/0267100 A1 | 12/2004 | Faupel et al. |
| 2005/0017864 A1 | 1/2005 | Tsoukalis |
| 2005/0020887 A1 | 1/2005 | Goldberg |
| 2005/0021372 A1 | 1/2005 | Mikkelsen et al. |
| 2005/0027400 A1 | 2/2005 | Wang et al. |
| 2005/0027562 A1 | 2/2005 | Brown |
| 2005/0033120 A1 | 2/2005 | Cohen |
| 2005/0033127 A1 | 2/2005 | Ciurezak et al. |
| 2005/0038674 A1 | 2/2005 | Braig et al. |
| 2005/0043965 A1 | 2/2005 | Heller et al. |
| 2005/0049464 A1 | 3/2005 | Lassers et al. |
| 2005/0054940 A1 | 3/2005 | Almen |
| 2005/0055242 A1 | 3/2005 | Bello et al. |
| 2005/0059895 A1 | 3/2005 | Brown |
| 2005/0060194 A1 | 3/2005 | Brown |
| 2005/0065760 A1 | 3/2005 | Murtfeldt et al. |
| 2005/0066969 A1 | 3/2005 | Rick et al. |
| 2005/0080652 A1 | 4/2005 | Brown |
| 2005/0086083 A1 | 4/2005 | Brown |
| 2005/0114444 A1 | 5/2005 | Brown et al. |
| 2005/0172021 A1 | 8/2005 | Brown |
| 2005/0172022 A1 | 8/2005 | Brown |
| 2005/0228883 A1 | 10/2005 | Brown |
| 2005/0235060 A1 | 10/2005 | Brown |
| 2005/0256739 A1 | 11/2005 | Brown |
| 2005/0273509 A1 | 12/2005 | Brown |
| 2006/0004611 A1 | 1/2006 | Brown |
| 2006/0010014 A1 | 1/2006 | Brown |
| 2006/0080152 A1 | 4/2006 | Brown |
| 2006/0089969 A1 | 4/2006 | Brown et al. |
| 2006/0100910 A1 | 5/2006 | Brown |

FOREIGN PATENT DOCUMENTS

| | | |
|---|---|---|
| DE | 4315532 | 12/1992 |
| EP | 462466 | 12/1991 |
| EP | 94907355 | 2/1996 |
| EP | 483595 | 5/2001 |
| EP | 700302 | 9/2001 |
| EP | 1144028 | 10/2001 |
| EP | 505479 | 12/2001 |
| EP | 1164530 | 12/2001 |
| EP | 1338295 | 8/2003 |
| EP | 1437674 | 7/2004 |

(56) References Cited

FOREIGN PATENT DOCUMENTS

| | | |
|---|---|---|
| FR | 2831300 | 10/2001 |
| GB | 2218831 | 11/1989 |
| GB | 2309644 | 6/1997 |

* cited by examiner

FIG. 3 — Tools & Info: Meal Times, Provider Info, Regimen, bG Corrections, bG Targets, Current Weight, Carb Calculator, Main Menu (labeled 24)

FIG. 4 — Meal Times

| | Meal | Entry |
|---|---|---|
| Breakfast | 7:00 am | 7:00 am |
| Lunch | 12:00 pm | 12:00 pm |
| Supper | 6:00 pm | 6:00 pm |
| Bedtime | -- | 11:00 pm |

View: Usual | Today
Test PostMeal bG 1 hr after meal start
Done

FIG. 5 — Regimen

TDD: 41 Units
Health/Activity: Usual

| | B | L | S | Bed |
|---|---|---|---|---|
| Lispro | 9 | 7 | 7 | -- |
| NPH | 11 | -- | -- | 7 |

View: Usual | Today
Insulin Units: Whole | Half
Done

FIG. 6 — Regimen

TDD: 34 Units
Health/Activity: Light Exercise

| | B | L | S | Bed |
|---|---|---|---|---|
| Lispro | 7 | 6 | 6 | -- |
| NPH | 9 | -- | -- | 6 |

View: Usual | Today
Insulin Units: Whole | Half
Done

FIG. 7 — bG Corrections

| bG Bin (mg/dl) | B/L/S | Mid Sleep | Post/Late |
|---|---|---|---|
| <80 | -1 | | |
| 80-120 | 0 | | |
| 121-140 | 0 | 0 | |
| 141-160 | 1 | 0 | 0 |
| 161-180 | 1 | 1 | 0 |
| 181-200 | 2 | 1 | 1 |
| 201-220 | 3 | 2 | 1 |
| 221-240 | 3 | 3 | 2 |
| >240 | 4 | 3 | 3 |

Done

FIG. 8 — bG Targets

Your bG goal is at or within the target range set by your health care provider.

| | | | |
|---|---|---|---|
| PreMeal | 80 | to 120 | mg/dl |
| Bedtime | 110 | to 140 | mg/dl |
| MidSleep | 80 | to 100 | mg/dl |
| PostMeal | 110 | to 140 | mg/dl |

Done

FIG. 9 — Tools & Info / Current Weight

Weight Unit: lb | kg
HCP-set weight: 150 lb
Current weight: 150 lb
Last Update: 4/21/04
Done

DEVICE AND METHOD FOR INSULIN DOSING

RELATED APPLICATIONS

This application claims priority U.S. application Ser. No. 11/422,639, filed Jun. 7, 2006 titled "DEVICE AND METHOD FOR ADJUSTING INSULIN DOSING" which claims priority to U.S. Provisional Patent Application Ser. No. 60/689,166, filed Jun. 9, 2005, to Zivitz et al., titled "ACCU-CHEK ADVISOR INSULIN GUIDANCE SOFTWARE HEALTHCARE PROFESSIONAL'S GUIDE," U.S. Provisional Patent Application Ser. No. 60/689,751, filed Jun. 9, 2005, to Zivitz et al., titled "ACCU-CHEK ADVISOR INSULIN GUIDANCE SOFTWARE USER'S GUIDE," U.S. Provisional Patent Application Ser. No. 60/689,703, filed Jun. 9, 2005, to Zivitz et al., titled "INSULIN DOSING FOR ACUTE PHYSIOLOGICAL SHIFTS," U.S. Provisional Patent Application Ser. No. 60/689,702, filed Jun. 9, 2005, to Zivitz et al., titled "INSULIN DOSING ALTERATIONS FOR DEVIANT INSULIN INJECTIONS," and U.S. Provisional Patent Application Ser. No. 60/689,303, filed Jun. 9, 2005, to Zivitz et al., titled "INSULIN DOSAGE ADJUSTMENTS FOR HIGH BLOOD GLUCOSE READING," the priority of which and disclosures of which are each expressly incorporated by reference herein.

FIELD OF THE INVENTION

The present invention relates generally to the administration of insulin in diabetics. More particularly, the present invention relates to a device and method that provides insulin dosage alterations for various conditions.

BACKGROUND AND SUMMARY

The art of self-care for a patient with Type-1 diabetes typically involves an assortment of professional Health Care counseling, hard-copy guide sheets provided by a Health Care Professional, self-care reading material and improvisation based on well established general principles of how the endocrine system operates. However, this knowledge is hard won and not easily put into practice by patients with Type-1 diabetes.

A person with type 1 diabetes will typically die well within a year without insulin. Even still, not all such persons are willing to make alterations to their (necessary—life sustaining) doses. They administer fixed fast-acting insulin doses in conjunction with meals and rarely, if ever, make alterations to those doses. Additionally, they administer doses of a slower-acting insulin to contend with their background needs (e.g., mobility) not associated with meals.

By contrast, for persons with type 2 diabetes: approximately only 30% of these persons inject insulin, more of those persons can benefit from injecting insulin, and not all of these persons need insulin, meaning diet, exercise and oral "meds" may suffice.

Accordingly, a device and method are provided that automates insulin dosing advice.

According to one aspect of the present invention, a device for providing improved drug dosing advice to a patient is provided. The device being a portable, handheld and battery powered device comprising: an evaluation and interpretation facility comprising a processor for executing a program, a memory for storing a program to be executed by the processor and for storing and retrieving data used by the program, a display for displaying data and instructions to the user, and a human interface for entering data, and instructions stored on the memory as part of the program. When the program is executed by the processor, it causes the evaluation and interpretation facility to: determine a first expected dose of the drug; determine a first actually administered dose of the drug, determine whether the first actually administered dose differs from a first expected dose of the drug, determine a second expected dose of the drug; determine a second actually administered dose of the drug, determine whether the second actually administered dose differs from a second expected dose, and calculate a third expected dose on the basis of the first actually administered dose and the second actually administered dose when the first actually administered dose is determined to differ from the first expected dose and the second actually administered dose is determined to differ from the second expected dose.

Additional features of the present invention will become apparent to those skilled in the art upon consideration of the following detailed description of the presently perceived best mode of carrying out the invention.

BRIEF DESCRIPTION OF THE DRAWINGS

The detailed description of the drawings particularly refers to the accompanying figures in which:

FIGS. 3-15 are screens capable of being displayed on the PDA of FIG. 1.

DETAILED DESCRIPTION OF THE DRAWINGS

Figure 1:
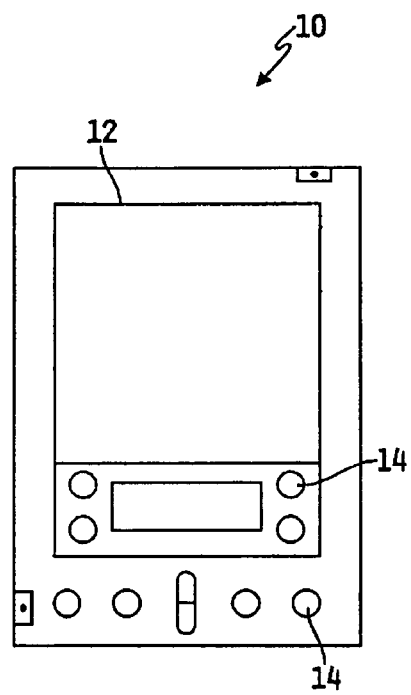
FIG. 1 is a PDA capable of providing insulin dosing advice.

A PDA 10 is shown in FIG. 1 for providing insulin dosing advice to a user. PDA 10 includes a screen 12, a plurality of input devices/human interfaces 14 (which may include screen 12), a processor (not shown), and memory (not shown). Examples of PDA's are handheld computing devices made commercially available by Palm, Inc. and Handspring. While the methods and programs described herein will be discussed as taking place through the use of PDA 10, it should be appreciated that various devices capable of performing the methods or executing the programs are envisioned as suitable alternatives to a PDA 10.

PDA 10 is selectively connected to a desktop application such as a PC or a printer. PDA 10 is additionally capable of downloading data to a web based server where the data can be reviewed by a health care professional. The connections may be wired or wireless.

The memory of PDA 10 stores programs thereon which are executed by the processor of PDA 10. The processor performs the functions of an evaluation and interpretation facility for executing a program. The memory of PDA 10 also stores data used by and/or retrieved by the programs. One such program is an interactive program for dispensing insulin dosing regimen advice.

A "regimen" consists of a battery of base doses, also referred to as usual doses. In the field of insulin dose therapy are two kinds of alterations of these usual doses: adjustments and supplements. "Adjustments" are defined as persistent changes to usual doses, and supplements are defined as temporary changes to usual doses.

This temporal contrast can be shown on the basis of an alteration to a usual dose that relates either to the current session (AKA entry) alone, in which case the alteration is a supplement. For an alteration that relates both to the current session and to a next (or further) session, the alteration is an adjustment.

Figure 2:
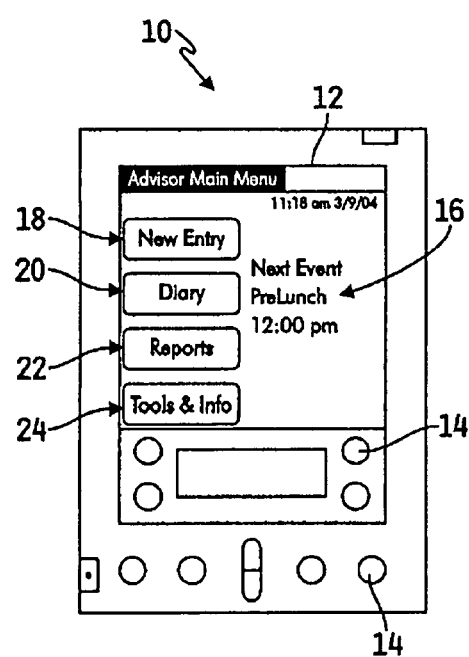
FIG. 2 is an example of a screen shown on the PDA of FIG. 1.

An opening screen shot for the insulin dosing program is shown running on a PDA 10 in FIG. 2. FIG. 2 shows a menu including an indication of a next scheduled injection, meal start, or pre-meal or bedtime entry 16. Additionally, the user is presented four buttons including New Entry 18, Diary 20, Reports 22, and Tools And Info 24. New Entry button 18 allows the user to enter new information relating to scheduled entries, injections, or meals. Diary button 20 allows a patient to review previous entries. Reports button 22 allows the user to create an on-screen report or a text exported report. Tools And Info button 24 allows the user to find information and review settings and tools.

The software allows a healthcare professional to assemble a prescription such that for each entry time, patients are provided with time sensitive advice and restrictions based upon the healthcare professional configured prescription. Furthermore, the software allows for each recommendation for each entry to vary according to the prescription, the entry time label, and patient's input. In general, a prescription includes usual doses for each time period at which a regiment dose is to be administered. The prescription further includes a plurality of dosing alterations for various factors, which are discussed below.

A pre-meal entry includes many pieces of information including a blood glucose result, an entry time label, a health/activity level, food intake information, insulin advice, actual insulin taken, physiological information, injection time, and meal time advice. The blood glucose result is typically received by either reading blood glucose results from a compatible blood glucose meter or from a numeric key pad on the screen used by the user to enter the blood glucose values. The software will check the time on the blood glucose result to make sure it is recent enough for actionable support or advice. When the blood glucose result is received from a compatible blood glucose meter, the result will have the time associated with the result as part of the received transmission. When the blood glucose result is received via the numeric keypad the user is either allowed to enter the time that the result was taken or the time of entry is used as the time the result was taken. In some embodiments, if the blood glucose result is entered via the numeric keypad and the time of the result is likewise entered via the keypad, the software requires that the time entered be within a defined range of when the entry is being inputted. For example, in such embodiment the software will require that if the reading was taken at 12:45 p.m. that it actually be entered into PDA 10 by 1:00 p.m. The advice and support available for each entry changes based upon the entry time label. This label allows the software to retrieve the correct prescription parameters for the entry time. Patients can also select physiological conditions that effect their insulin requirements, such as exercise, stress, menstrual status, and whether or not the patient is experiencing illness. Once such conditions are selected, the patient may enter a value related to that condition, select one of a set of pre-selected value associated with such conditions, or the value may be incorporated in the condition (e.g. light exercise or mild stress). The value may be a numerical value, such as to indicate a severity or level of the condition such as light, mild, etc., may be a yes or no, and may include words to describe the condition. The software uses prescription parameters that the healthcare professional sets to alter the patient's insulin advice based upon the entered patient conditions. The prescription parameters at least partially define how the patient conditions are interpreted by the software to alter dosing recommendations as discussed below.

The software also uses factors set by the healthcare professional in the prescription to provide food intake insulin supplements. These supplements allow patients to receive insulin advice for increased or decreased meal sizes and for snacks. The software consults the prescription to retrieve usual doses in an insulin regimen. It should be appreciated that the usual dose may be zero. It also retrieves any applicable prescription parameters that account for variances in normal levels of the blood glucose results, the health/activity factors, and food intake to provide patients with patient factor altered insulin advice.

Patients can also choose to accept the recommended insulin advice/expected insulin dose or to override the advised insulin dose. By disagreeing with the advised doses, patients can enter the insulin doses they actually plan to inject. The software then consults with the prescription for the insulin limits to guide how much patients can increase or decrease each insulin dose should they so choose. If the patient planned dose is outside of limits set in the program, alerts are generated and displayed to the user. Additionally, the number of the patient altered doses is logged and reported to the healthcare professional on the next instance of patient monitor data upload. After patients confirm insulin doses for actual use, the software uses the prescription and the patient's blood glucose results to display timing advice for when to administer the injection and when to ingest the related meal or snack.

Healthcare professionals are also able to provide lockouts for the advising software. The healthcare professional may define insulin limits and set notification items that help the patients manage their diabetes. The software uses these healthcare professional set limits to determine when to provide or suspend insulin therapy support. Notification items are generated when the input conditions and readings meet the set criteria such that the healthcare professional wishes to be notified thereof.

Many of the settings available to be changed by the healthcare professional, such as the prescription, are password protected to maintain the security of the prescription. This password limits the access to only allow the healthcare professional to make changes to the prescription and it ensures the privacy of the treatment plan. While the user or patient can view the prescription parameters by looking it up in the Tools And Info 24 section or creating text export, the user may be prohibited from making changes to the prescription via the password protection.

Diary button 20 provides a history of the patient's entries. The entries can be scrolled through or a calendar can be used to jump directly to a specific date. A diary day view lists entries that the patient has recorded for each day and the blood glucose results for each entry. Each entry can be selected to view details about the health and activity levels and the food intake, or to compare the advised insulin doses with the actually administered insulin doses.

Tools And Info section 24 of the software, shown in FIG. 3, provides meal time information. Before the patient can record entries, he/she uses the meal time screen, FIG. 4, to set up their schedule for meals and entries. Tools and Info section 24 may also give the patient's healthcare professional information. Here, the patient can look up contact information for their healthcare professional.

Tools And Info section 24 also allows the patient to look up his or her insulin regimen as shown in FIGS. 5 and 6. The patient can access a screen to view the insulin regimen prescribed by the healthcare professional. Patients can toggle the view to display the usual doses, which account for past adjustments, FIG. 5, or to view an altered regimen that includes supplements to account for changes in the health/activity state or food intake changes, FIG. 6.

The patient may also view a blood glucose correction table which displays scales set up in the prescription as shown in FIG. 7. The table defines the supplements in dosing that will be made in response to ranges of blood glucose readings reported to the device 10. The software automates these scales during a supported entry to automatically alter the recommended dose by the defined alteration amount. However, the patient may also access the screen to look up their blood glucose correction guidelines.

Blood glucose targets are also shown under Tools and Info section 24. As shown in FIG. 8, the blood glucose target screen displays the blood glucose goals set by a healthcare professional for the patient in the prescription. Patients may find it helpful to know the upper and lower limits of each target range.

As shown in FIG. 9, Tools and Info section 24 also provides a section where patients may enter weight updates. If set by the healthcare professional, the software reminds patients to enter weight updates at defined intervals, such as every two weeks.

Additionally, Tools And Info section 24 includes a carbohydrate calculator screen. The carbohydrate calculator screen displays a carbohydrate compensation tool that allows patients to enter carbohydrate grams and work with one or more insulin-to-carbohydrate ratios, morning or rest of day, set by a healthcare professional in the prescription, shown in FIGS. 10 and 11. These insulin-to-carbohydrate ratios are used by the prescription when increased or decreased food intake is entered by a patient to determine how much a usual dose will be supplemented to arrive at a recommended dose. The carbohydrate calculator screen is provided to a patient to give the patient an idea of how an inputted carbohydrate load will affect the recommended dose. While the patient is informed by this screen how the carbohydrate load will affect the recommended dose, it is for informational purposes only. The patient is not instructed to look up the supplement amount and unilaterally supplement their dose themselves.

The reporting features in the advising software allow a healthcare professional or a patient to review patient's entries and activities in two ways. The first way allows the creation of an on-screen report to review the information from the patient's PDA 10. Alternatively, the patient's PDA 10 is set up to create a text export that sends patient information from the PDA 10 to a healthcare professional's PC each time that a patient hot synchs their PDA 10 to a PC.

The software is set to categorize the received patient information and reports sent to the healthcare professional. The reports are organized such that those messages indicating severe readings are prioritized and sent to the top of the list to be first viewed by the healthcare professional.

Many different reports are available to be produced by the advising software. One such report is a date report that sorts the patient entries according to the date each entry was recorded. This report shows the number of entries for each date, the blood glucose result average for the day, and the total units of insulin that the patient recorded. A second type of report that is available is a diary report shown in FIG. 12. This report sorts the entry information according to the entry time label. This report shows the number of entries for each entry time within a selected date range specified by the healthcare professional. It also shows the average blood glucose result and the standard deviation for the selected blood glucose results. Furthermore, the diary report will list the lowest and highest blood glucose results for each entry time. A third type of report available from the software is a warnings report. The warnings report lists the insulin therapy alert messages that the patient has received during his or her entries, such as for exceeding a maximum daily dose of insulin. The healthcare professional may view the date and the entry time label for each alert message. A fourth type of report available from the advising software is the notifications report. The notifications report allows a healthcare professional to check the status of each notification item that has been enabled in the prescription by the healthcare professional. The healthcare professional can monitor high and low blood glucose results and review the percentage of blood glucose results outside of the target blood glucose ranges.

The healthcare professional works with the software to set up a prescription for an individual patient. The healthcare professional can define when and how the patient interacts with the software by specifying prescription parameters regarding the insulin regimen, blood glucose targets, blood glucose corrections, carbohydrate compensations, health/activity alterations and safety notifications. These settings allow the healthcare professional to set the usual doses, the timing of the usual doses, and the alteration factors that change the usual doses to arrive at the recommended doses.

In setting up the insulin regimen, the healthcare professional selects the types and amounts of insulin and the schedule when a patient will inject the insulin. The healthcare professional defines blood glucose target ranges, FIG. 8, for a patient to establish therapeutic goals to identify when the patient needs blood glucose corrections. The healthcare professional specifies the amount of insulin above or below the usual dose that the software recommends when the patient's blood glucose result is outside of his or her target range, FIG. 7.

The healthcare professional may also enable health and activity compensation to specify how the software responds to changes in the patient's health and activity levels, such as a mild illness, menstrual status, and exercise. Similarly, to how the carbohydrate intake supplements work, health and activity supplements allow insulin advice to be provided to recommend more or less insulin to compensate for changes in the patient's health and activity levels by receiving input regarding health and activity levels and converting that input into an alteration in the recommended dose.

Additionally, the healthcare professional may configure the prescription to define safety limits for insulin injections and blood glucose readings. The healthcare professional can specify when a patient should call the healthcare professional to keep the healthcare professional aware of the patient's ongoing insulin needs.

Figures 10, 11, 12, 13, 14, 15:
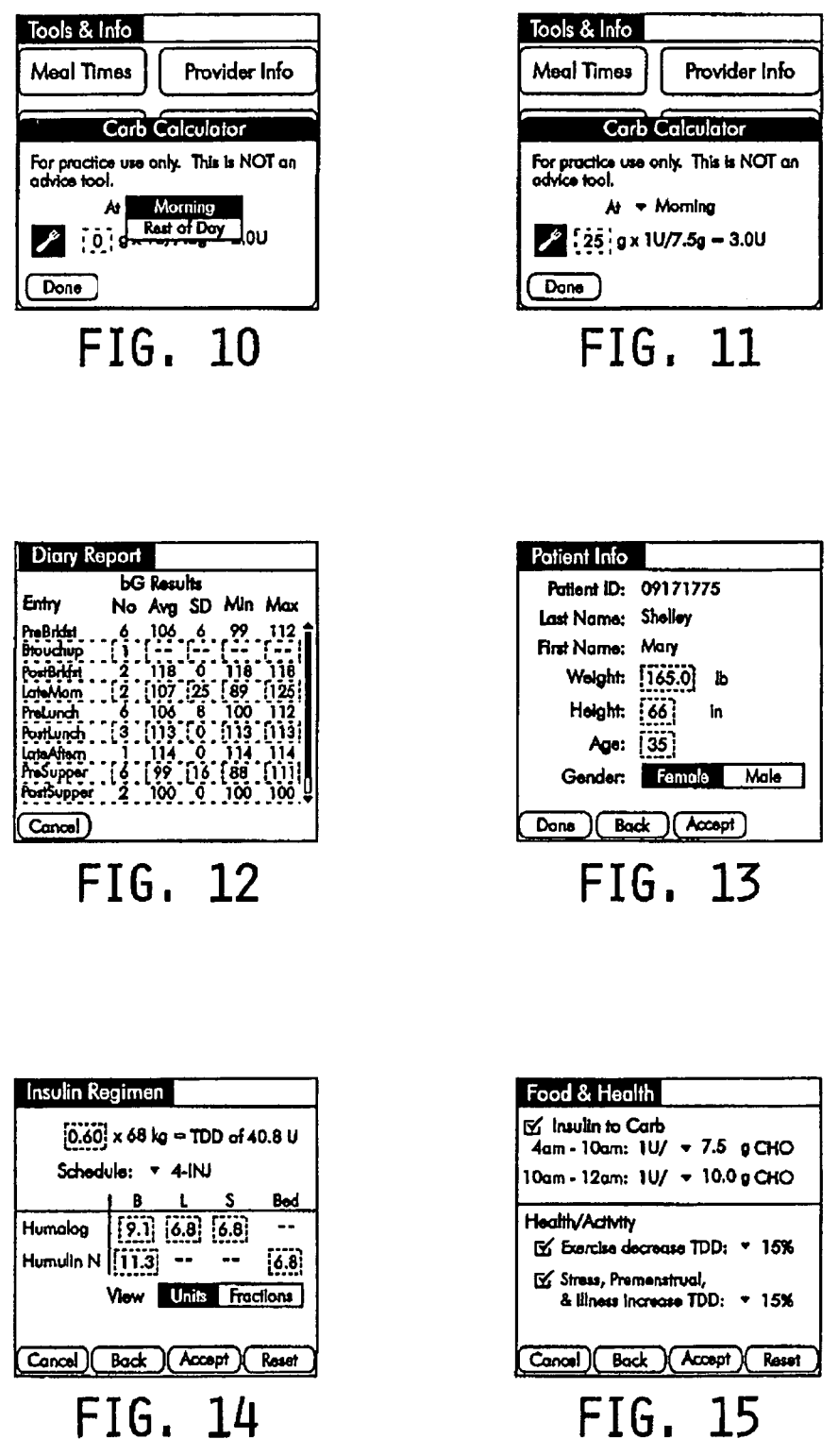

The healthcare professional also enters patient information such as height, weight, age and gender, FIG. 13. The healthcare professional may also enter information regarding whether the patient is pubescent or post-menopausal. The healthcare professional is also permitted to define a change in the insulin dose factor for said pubescent or post-menopausal patients. For patients identified as pubescent the healthcare professional is also permitted to enter information regarding the Tanner stage, stage of pubescence, of the patient and to set insulin dose factors specific to individual Tanner stages.

In setting up an insulin regimen, the software starts by allowing the health care provider to select specific insulin types to be administered. The software then utilizes the patient's weight and a prescribed insulin dose factor to determine a total daily dose of insulin for the specific patient, as shown in FIG. 14. The insulin regimen then allows the healthcare professional to select an injection schedule for patients, such as a four injection schedule, which would include a breakfast time, lunchtime, suppertime, and bedtime injections. Once the schedule is selected/set up, the healthcare professional is presented with a table that allows the healthcare professional to select the specific insulin amounts to be administered at each of the injection times.

The healthcare professional is also provided with the screen to define the blood glucose target ranges, FIG. 8. The blood glucose target range screen also allows the healthcare professional to define a low and high range for the blood glucose readings at either one or two hours after each of the prescribed meal start times. The healthcare professional is also enabled to assemble a table that determines what insulin supplements or adjustments to the usual dose are to be made in response to a blood glucose reading outside of the target ranges, FIG. 7.

The healthcare professional configures the insulin dose supplements for changes in food intake and changes in health factors, FIG. 15. A food and health screen allows the healthcare professional to control the insulin supplements for food variations and also insulin supplements for the health and activity variations.

As seen in FIG. 15, the healthcare professional may select different insulin-to-carbohydrate ratios to alter for food variations at different defined times of the day. Similarly, the healthcare professional may choose to define or enable alterations for health and activity changes and may choose the magnitude of the alteration factors therefor.

Most of the screens and features that are present for the healthcare professional have analogous screens and inputs for the patient. In Tools And Info section 24 of the software, the patient inputs the times they typically start eating breakfast and supper, as shown in FIG. 4. Using the meal times input by the patient, and the blood glucose measuring times being either one or two hours after a meal that is set by the healthcare professional, the advising system provides the patient with the times when blood glucose readings should be taken. Additionally, by inputting actual meal/bed injection times, the software alters later expected meal and injection times. For example, if a patient has a scheduled breakfast dose time of 7:00 a.m., a scheduled lunch dose time of 12:00 p.m., and informs the software that the actual breakfast dose time was 7:30 a.m., the software pushes out the scheduled lunch dose time to 12:30 p.m. to maintain the desired 5 hour separation between breakfast and lunch doses. In addition to inputting meal dose times, the patient may also input the time of a bed time dose.

Also in Tools And Info section 24 the patient may view the regimen prescribed by the healthcare professional. The patient may choose to view the usual prescription which incorporates past adjustments, FIG. 5, or the prescription for the current day, FIG. 6, which incorporates any of the supplements for the health/activity states.

Additionally, the patient may view the blood glucose correction screen, FIG. 7. The blood glucose correction screen displays the blood glucose elements specified by the healthcare professional on a blood glucose correction scale screen in the prescription. The patient may only view information on the screen and is not permitted to modify the values. The screen shows the insulin supplements which correspond to specific blood glucose readings at the different times when blood glucose test times are prescribed. Additionally, the patient may view the blood glucose target ranges, FIG. 8, which are set up by the healthcare professional on a blood glucose target screen.

A diary detail screen provides a summary of the information displayed during the entry. This information includes both the blood glucose result and physiological conditions entered by the patient, as well as the insulin therapy advice and feedback provided by the software. The patient sees the diary detail after completing entries. The diary detail screen can also be accessed by selecting an entry on the diary day screen. The diary detail screen includes an entry time label, a health and activity level for the entry, actually taken (administered) insulin doses, and an indication of whether the blood glucose result is above, within or below a target. The actual blood glucose results for the entry, indications of whether notes regarding the entry are available, and indications whether the food intake was above, below, or within the usual amounts are also available.

Patient entries regarding administered insulin injection times may alter subsequent scheduled injection times. For example, with prescriptions containing an intermediate acting insulin, if a patient's scheduled bedtime entry is 11 PM, the patient is provided with a window of up to an hour on either side in which to make that entry. If the patient records the bedtime entry at 11:30, the software identifies the patient's actual injection time as 11:30 PM. Because the patient's bedtime injection is 30 minutes after the scheduled time, the software will move the next stage pre-breakfast entry time later by 30 minutes, and the software will alert the patient of the change. Such movement helps maintain a desired eight hour time span between a bedtime and pre-breakfast insulin injection. Likewise, injecting the pre-breakfast insulin dose before or after the scheduled time can effect pre-lunch and pre-supper insulin injections.

To update meal entry times the software identifies three pieces of information. First, the software identifies the scheduled time for the pre-breakfast insulin injection which is obtained from the times the patient set up on the mealtime screen. Second, the software identifies when the patient actually injects the pre-breakfast usual dose of insulin. This time is displayed during the pre-breakfast entry as injection advice indicating when he/she should inject the insulin dose. Third, the software identifies the scheduled times for the pre-lunch and pre-supper blood glucose test times. These test times are set up on the mealtimes according to the breakfast and supper mealtimes the patient specifies.

The software compares the scheduled time for pre-breakfast insulin injections to the actual injection time. Both the pre-lunch and pre-supper times update to maintain the original interval of time between the pre-lunch/pre-supper time and the pre-breakfast entry time shown on the mealtime screen. If the patient injects the pre-breakfast usual insulin dose more than five minute before or after a scheduled time, the software shifts the pre-lunch and pre-supper times by the same amount. An alert message is also generated to display the updated time for the next scheduled entry which is pre-lunch in the provided example. The patient is then provided a mealtime screen that shows the updated meal and entry times for the patient. Alternatively, the patient is shown the main menu that displays a "next event" field.

The information entry process for a patient includes four main screens: A new entry screen (not shown), where patients can enter their blood glucose result, a control result, or indicate that they wish to record an entry without entering a blood glucose result. The second main screen is an entry input screen (not shown). Here, the software provides feedback on a patient's blood glucose result and allows patients to specify conditions impacting their insulin advice, such as their current health, activity state, and carbohydrate intake. The third main screen is the entry advice screen (not shown). The entry advice screen retrieves usual insulin doses from the regimen prescribed by the healthcare professional, blood glucose corrections and any conditions patients enter on the previous screens, and the software displays insulin dose advice. On the entry advice screen the patient is also invited to agree with the insulin advice provided or to disagree, and then enter the insulin dose(s) they actually intend to inject.

The fourth main screen is the entry insulin screen (not shown). This final screen in the entry allows patients to confirm their insulin dose and it also displays meal and insulin timing advice.

When entering the intended carbohydrate intake, on the second main screen, a carbohydrate compensation algorithm can come into effect if the patient-declared carbohydrate intake excursion or increment exceeds the defined carbohydrate limits. In such a case, the currently declared carbohydrate intake is compared to the defined carbohydrate limits and then the insulin-to-carbohydrate ratio is applied to place the increment within the carbohydrate limits. In the event that the declared carbohydrates are above the carbohydrate limit the patient will also be provided with a warning indicating that their declared carbohydrate intake is above the prescribed carbohydrate limit, and that they should reduce the amount of carbohydrates they are planning to ingest at the current meal. Similar programming exists for events where the declared carbohydrate intake is deemed too low. The patient then chooses whether or not to alter their carbohydrate intake or proceed with the previously entered carbohydrate intake.

The software then progresses to an entry advice screen that reinforces the entry time label and the blood glucose result for the entry and displays advised insulin doses. The screen indicates both the adjusted usual insulin doses for each type of prescribed insulin and any supplemental doses that are recommended for each type of insulin based upon the change factors, and then displays the total recommended dose that is the sum of the adjusted usual dose and the supplemental dose.

The patient is also invited to agree or disagree with this advice. If the patient agrees with the insulin advice and intends to take the amount of insulin shown in the total column, he/she chooses "agree." If the patient does not agree with the advice, he/she taps "disagree." This brings up a screen instructing the patient to enter the actual dose that he/she intends to take. When a patient taps the "accept" to continue with the entry, the software will compare the patient's actual intended dose to the insulin limits calculated for the entry. An alert message will appear to tell the patient when an insulin dose is above or below an insulin limit. The alert message further provides the patient with the option to return to the interaction insulin screen and change the insulin dose. Alternatively, the patient is allowed to choose that they do not wish to change the actual insulin dose and they plan on proceeding with their previously entered dose. In the event that the patient chooses to proceed with a dose that is outside of predefined limits, a notice or warning is created. Furthermore, under certain circumstances predefined by the healthcare professional, such as exceeding the total daily dose or the patient's blood glucose reading being outside of a desired range, notifications or warnings are transmitted to the patient and potentially to the healthcare professional or another third party via e-mail or other communication.

As part of the functionality allowing the patient to disagree with recommended doses, the software runs an algorithm that detects consistent deviation from recommended doses. More specifically, if a patient disagrees with a dose on a first day, for example, Monday, and specifically the pre-breakfast entry, and likewise disagrees on a second day, for example, Tuesday, with the breakfast entry again, the algorithm will note the consistent deviation from a recommended dose and adjust the recommended dose to be the average of the two patient altered doses. Such adjustment will be performed by the algorithm taking into account the recommended usual dose and any alteration present in the altered recommended dose. For example, if a patient indicates typical health and exercise status on both Monday and Tuesday at the pre-breakfast dosing times then the recommended doses for Monday and Tuesday pre-breakfast are possibly equal. If the user has indicated an administered dose that differs from the recommended dose at pre-breakfast of both Monday and Tuesday, the algorithm will know that the usual dose for the pre-breakfast time should be adjusted to be the average of the two patient inputted administered/actual doses. Similarly, if the pre-breakfast dosings for typical conditions are being followed by the patient, but the recommended dosings on days when there is increased exercise are being altered by the patient, the software looks for two consecutive increased exercise days on which the pre-breakfast dose is altered by the patient. In such an event, the algorithm adjusts the factor by which the usual dose is altered for exercise such that the recommended dose for pre-breakfast on days with increased exercise is the average of the two doses that were altered by the patient. It should be noted that the two consecutive increased exercise days do not have to be consecutive calendar days. For example, if there is increased exercise on Monday and the patient rejects the recommended pre-breakfast dose, followed by normal exercise on Tuesday and the patient accepts the recommended pre-breakfast dose, followed by increased exercise on Wednesday and the patient rejects the recommended pre-breakfast dose, then the algorithm recognizes that with respect to days with increased exercise, the previous two such days are associated with the patient rejecting the recommended pre-breakfast dose. Accordingly, the alteration factor associated with exercise will be adjusted to allow the recommended pre-breakfast dose to be the average of the previous two actually administered pre-breakfast doses under the defined conditions (the average of Monday and Wednesday).

More generally, when making alterations in the recommended doses, the algorithm considers past doses taken and recommendations that were provided when the patient was experiencing health and activity levels (or states) similar to the current levels (or states) for which a recommendation is being generated. As another example, if a patient indicates that she is starting her menstrual cycle, the algorithm takes into account the doses recommended and taken the last time that the patient indicated that she was starting her menstrual cycle as well as considering the blood glucose control that resulted from the recommended/taken doses on those days.

Another example usual dose alteration algorithm deals with when a low blood glucose level is received by the dosing program, by example of a low blood glucose received before lunch. In such an event, the algorithm adjusts the breakfast bolus dose on the following day. More generally, the algorithm will analyze the dose administered prior to a low blood glucose reading to determine what factor of the earlier taken dose needs to be adjusted. Using historical recommended doses, historical actual doses, historical patient factors, the usual dose, alterations, and patient factors for the prior dose, all of which are stored in PDA 10 or another computing device, the algorithm determines which, if any, of the usual doses, the alteration doses, or supplemental doses need to be altered.

The algorithm also watches for unscheduled insulin doses. If a patient indicates that he has made an injection at a time when the advising system has not recommended a dose, the administered dose is labeled as an unscheduled dose. Similarly to how the algorithm processes repeated doses that deviate from the recommended doses, repeated unscheduled doses at similar times under similar physiological conditions result in the adjustment of the expected doses or the addition of a regularly scheduled extra dose.

Additionally, the software has the ability to require that a blood glucose reading be entered, either into a blood glucose monitor or to be keyed into the advisor, within a defined window around an expected time for the blood glucose reading. For example, if the advisor system expects a blood glucose reading at noon, the advisor system can define a window from 11:00 a.m. to 1:00 p.m. in which the patient is required to manually enter a blood glucose reading or to have the reading taken on a blood glucose meter capable of noting the time and beaming the results to the advisor system. Failure to enter a reading within the window causes the advisor system to label the entry as non-conforming and prevent the patient from receiving an insulin dose recommendation. Requiring that the blood glucose reading be entered within the window or being able to show that the reading was taken at a specific time by having the results beamed to the advisor system provides increased likelihood that the reading was actually taken rather than being fabricated by the patient.

In one embodiment, the ability of the algorithm to quickly alter the recommended doses is aided by requesting many pre- and post-meal blood glucose readings. In, for example, a first week of use by a patient, the advising system requests all possible pre- and post-meal blood glucose readings, with the possible exception of a 3-am reading, and uses these readings to customize the recommended regimen. A low blood glucose reading causes adjustment of the regimen of the next day. A high blood glucose reading requires the previously discussed two day repetition to cause adjustment of the regimen. After the algorithm has received enough data, for example, a week, post-meal blood glucose readings are only conditionally requested. Such conditional requests may be requested to verify that dose alteration levels are properly set or when a new health or activity condition is defined or selected by the patient.

Although the invention has been described in detail with reference to certain preferred embodiments, variations and modifications exist within the spirit and scope of the invention as described and defined in the following claims.

The invention claimed is:

1. A device for providing improved drug dosing advice to a patient, the device being a portable, handheld and battery powered device and the device comprising:
   an evaluation and interpretation facility comprising a processor for executing a program,
   a memory for storing a program to be executed by the processor and for storing and retrieving data used by the program,
   a display for displaying data and instructions to the user,
   a human interface for entering data, and
   instructions stored on the memory as part of the program such that when the program is executed by the processor causes the evaluation and interpretation facility to:
   determine a first expected dose of the drug;
   determine a first actually administered dose of the drug,
   determine whether the first actually administered dose differs from a first expected dose of the drug,
   determine a second expected dose of the drug;
   determine a second actually administered dose of the drug,
   determine whether the second actually administered dose differs from a second expected dose, and
   calculate a third expected dose on the basis of the first actually administered dose and the second actually administered dose when the first actually administered dose is determined to differ from the first expected dose and the second actually administered dose is determined to differ from the second expected dose;
   wherein the device is further configured to upload dosing history to a healthcare professional computer.

2. The device of claim 1, wherein the instructions further cause the device to display the third expected dose to the user via the display.

3. The device of claim 1, wherein the evaluation and interpretation facility is able to calculate the third expected dose by averaging the first actually administered dose and the second actually administered dose.

4. The device of claim 1, wherein the first expected dose is zero.

5. The device of claim 1, wherein the second expected dose is zero.

6. The device of claim 1, wherein the first expected dose is equal to the second expected dose.

7. The device of claim 6, wherein the evaluation and interpretation facility is able to define the third expected dose to be equal to the first expected dose if the first expected dose is equal to the actually administered first dose or if the second expected dose is equal to the actually administered second dose.

8. The device of claim 1, wherein the first and second expected doses are each provided to the evaluation and interpretation facility via an administering plan set up by a health care professional and stored in the memory.

9. The device of claim 1, wherein the first and second doses are each calculated by the evaluation and interpretation facility by utilizing previously determined differences between expected and actually administered doses.

10. The device of claim 1, wherein the doses are doses of insulin and the expected doses assist the patient in controlling diabetes.

11. The device of claim 1, wherein the first expected dose is for a defined time on a first day, the second expected dose is for the defined time on a second day, and the third expected dose is for the defined time on a third day.

12. The device of claim 11, wherein the first and second days are consecutive days.

13. The device of claim 11, wherein the first and second days are days when the patient experiences similar physiological conditions.

14. The device of claim 13, wherein the instructions further provide that the evaluation and interpretation facility determines the third expected dose by:
   defining a value for a physiological condition as a normal value and define a usual dose associated with the normal value of the physiological condition;
   receiving indications of a value of the physiological condition of the patient;
   determining if the value of the physiological condition of the patient is equal to the defined normal value;

defining the usual dose as the first expected dose if the value of the physiological condition of the patient is equal to the defined normal value; and defining first expected dose when the value of the physiological condition of the patient is not equal to the defined normal value by determining a given dose administered in the past when the value of the physiological condition was similarly not equal to the defined normal value and defining the first expected dose as equal to the given dose administered in the past.

15. The device of claim 14, wherein the physiological condition is selected from the group including menstrual status, exercise level, stress level, and illness status.

16. The device of claim 15, wherein the memory stores a set of alterations corresponding to each potential value of the physiological condition.

17. The device of claim 14, wherein the display is able to display both the usual dose and the given dose administered in the past when the value of the physiological condition of the patient is not equal to the defined normal value.

18. The device of claim 14, wherein the normal value is defined as a range of possible values.

19. The device of claim 14, wherein the instructions further cause the evaluation and interpretation facility to:
instruct the patient to either 1) agree to the administration of the third expected dose or 2) to disagree with the administration of the third expected dose and input a third actually administered dose.

* * * * *